United States Patent [19]

Souma

[11] Patent Number: 5,467,772
[45] Date of Patent: Nov. 21, 1995

[54] AUTOMATIC SPHYGMOMANOMETER

[75] Inventor: Takahiro Souma, Fujinomiya, Japan

[73] Assignee: Terumo Kabushiki Kaisha, Tokyo, Japan

[21] Appl. No.: 76,631

[22] Filed: Jun. 15, 1993

[30] Foreign Application Priority Data

Jun. 16, 1992 [JP] Japan ................... 4-156506

[51] Int. Cl.⁶ ........................................ A61B 5/00
[52] U.S. Cl. ...................... 128/680; 128/681; 128/685; 128/682
[58] Field of Search ..................... 128/677–686

[56] References Cited

U.S. PATENT DOCUMENTS

| | | |
|---|---|---|
| 4,566,463 | 1/1986 | Taniguchi et al. ............... 128/682 |
| 4,587,974 | 5/1986 | Link ................................. 128/685 |
| 4,638,810 | 1/1987 | Ramsey, III et al. . | 
| 4,754,761 | 7/1988 | Ramsey, III et al. . |
| 5,027,823 | 7/1991 | Sanaka ............................ 128/685 |
| 5,052,397 | 10/1991 | Ramsey, III et al. . |
| 5,054,495 | 10/1991 | Uemura et al. .................. 128/650 |
| 5,143,077 | 9/1992 | Kobayashi ....................... 128/677 |
| 5,220,925 | 6/1993 | Hishada .......................... 128/686 |

FOREIGN PATENT DOCUMENTS

| | | |
|---|---|---|
| 0423006 | 4/1991 | European Pat. Off. . |
| 00423006 | 4/1991 | European Pat. Off. ........ 128/685 |
| 2759119 | 8/1978 | Germany . |
| 3-68689 | 10/1991 | Japan . |

Primary Examiner—Lee S. Cohen
Assistant Examiner—Robert L. Nasser, Jr.
Attorney, Agent, or Firm—Burns, Doane, Swecker & Mathis

[57] ABSTRACT

A small and power-saving automatic sphygmomanometer constructed of minimum of parts. This automatic sphygmomanometer which inflates a pressure cuff to a value higher than that of one's maximum blood pressure and measures the blood pressure in the process of deflation is comprised of a cuff, air pump connected to the cuff, constant-rate pressure reducing valve for automatically adjusting a cuff pressure reducing velocity to be constant regardless of cuff pressure, exhaust valve for exhausting the air from the cuff, and controller for controlling open/close of the exhaust valve.

18 Claims, 6 Drawing Sheets

FIG. 6

AUTOMATIC SPHYGMOMANOMETER

BACKGROUND OF THE INVENTION

The present invention relates to an automatic sphygmomanometer and, more particularly, to an automatic sphygmomanometer capable of measuring blood pressure in a deflating process after a cuff pressure is inflated to a value higher than that of the maximum blood pressure of a patient.

A well-known automatic sphygmomanometer technique in measuring maximum and minimum blood pressure is one in which the cuff pressure is inflated to a value higher than that of maximum blood pressure by an electric-powered pump, after which the cuff pressure and cuff pulse wave are measured by a pressure sensor, and presence of Korotkoff sounds (hereinafter referred to as "K sounds") is detected, while the cuff pressure is continuously reduced.

In this method, when the cuff pressure has been inflated to a value higher than that of one's maximum blood pressure, the pneumatic pressure (an air pressure) for generating a cuff pressure is high in comparison with the case where the cuff pressure is low. Accordingly, since the velocity of the air which is released via a nozzle of an exhaust valve connecting to the cuff is increased, and the dynamic pressure becomes large, a rather large amount of torque is required to close the exhaust valve once it has been opened. As a result, a large solenoid, consuming a large amount of electric power or another suitable unit, is needed.

On the other hand, in a sphygmomanometer which needs to be constructed as compact as possible, since the volume of a case is limited, only a driving power source having a small capacity, such as a size AA battery can be used even when a solenoid is used.

Accordingly, in order to suppress the exhaust air velocity caused by high pressure and obtain a constant deflating velocity, a plurality of pneumatic resistors and valves for switching those resistors or a plurality of solenoids having small electric power requirement which are respectively incorporated with the valves can be used. Furthermore, in order to maintain a deflating amount of the cuff pressure, for both cases where the cuff pressure is high and low, the exhaust valve open duration is changed according to the cuff pressure. When the cuff pressure is high, the duration for opening the exhaust valve is shorten, while when the cuff pressure is low, the duration is made longer That is, the duration for opening the exhaust valve is controlled substantially in inverse proportion with respect to the cuff pressure.

SUMMARY OF THE INVENTION

However, in the conventional construction, a plurality of pneumatic resistors, switch valves attaching to the pneumatic resistors, and valves pairing with those switch valves are required, thus resulting in a problem which requires that these units be installed in the limited space of the case. When a mechanism which variably changes a pneumatic resistance by detecting a cuff pressure and changing an orifice by using a needle valve is provided, the problem is such that the size of the apparatus becomes considerably large. The control means which moves the valve at high speed and controls the exhaust valve based on the duration for opening the exhaust valve in accordance with the cuff pressure must control the solenoid valve being responsibly operated. However, it is not realistic since there is no such solenoid valve.

Accordingly, in the light of the above drawbacks, it is an object of the present invention to provide a compact and energy-saving automatic sphygmomanometer with a least numbers of elements, which inflates a cuff to a value of the maximum blood pressure of a patient and measures a blood pressure in a deflating process.

According to the present invention, the foregoing object is attained by an automatic sphygmomanometer which inflates a cuff pressure to a value higher than that of one's maximum blood pressure and measures the blood pressure in a deflating process, comprising: a pressure cuff; air pressurization means connected to the pressure cuff to pressurize the cuff by pumping an air into the cuff; a pressure reducing valve connected to the cuff for automatically adjusting a cuff pressure reducing exhaust velocity to a constant rate regardless of the cuff pressure; an exhaust valve for connecting to the exhaustion side of the pressure reducing valve and exhausting the air from the cuff; and control means for controlling the open and close the exhaust valve.

With the above arrangement, since a constant-rate pressure reducing valve decreases a pneumatic velocity which is released from the exhaust valve to the outside and the dynamic pressure is reduced when the cuff pressure is high, a cuff pressure reduction rate is automatically adjusted to be constant without regard to the cuff pressure, the exhaust valve connecting to the pressure reducing valve and releasing the air from the cuff can be small and energy-saving type.

That is, the pneumatic resistance is large when the cuff pressure is large, while it is small when the cuff pressure is small, since an opening area of the pressure reducing valve which connects the pneumatic circuit and the outside is changed by the pressure of the pneumatic circuit including the cuff. Since the unit is installed in a small limited space, the exhaust valve can be driven by using a solenoid valve requiring a low electric power source such as a battery.

Furthermore, since a pressure reduction rate can be simultaneously controlled as being constant, a fixed duration for opening the valve can be used until the cuff pressure becomes considerable low. Still further, since the exhaust opening duration is proportional to the current pressure, control of an arbitrary pressure reducing pressure becomes easy.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated and constitute a part of the specification, illustrate embodiments of the invention and, together with the description, serve to explain the principles of the invention.

DESCRIPTION OF THE PREFERRED EMBODIMENTS

Preferred embodiments of the present invention will now be described in detail in accordance with the accompanying drawings.

Figure 1:
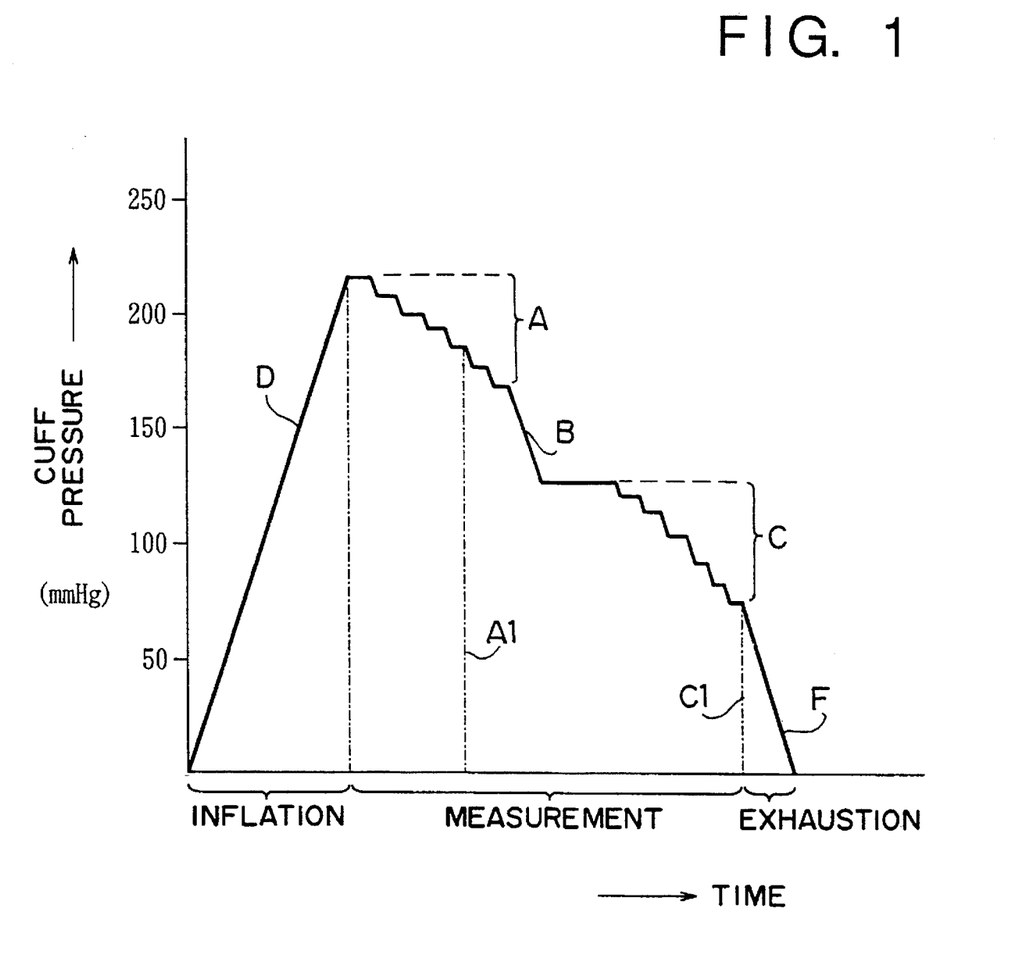
FIG. 1 is a diagram for explaining the relationship between a cuff pressure (in a vertical axis) and measured time (in a horizontal axis) in a blood pressure measuring method.

FIG. 1 is a diagram for indicating the relationship between a cuff pressure (in a vertical axis) and measured time (in a horizontal axis) in a sphygmomanometer, and expressing an example of the operation in the automatic sphygmomanometer which is described later.

Once the cuff is set on the portion to be measured, e.g. a patient's arm, the cuff pressure is inflated to a value higher than the patient's maximum blood pressure by an electric-powered pump. As indicated the characteristic line D in FIG. 1, this inflation occurs substantially linearly toward the value higher than the patient's maximum blood pressure and a measured maximum blood pressure A1 is obtained by measuring a cuff pressure and detecting K sounds while the cuff pressure is reduced in a plurality of stages (Range A). Subsequently, the cuff pressure is reduced a considerably large amount in order to shorten the measuring time (Range B), and again deflated in a plurality of stages (Range C), and then the cuff pressure when the K sound is extinguished is obtained as a measured minimum blood pressure C1. Then, the cuff pressure is completely released (Range F). The operation of releasing the cuff pressure in the plurality of stages can be performed by the exhaust valve which is opened/closed by a solenoid such as an actuator.

Figure 2:
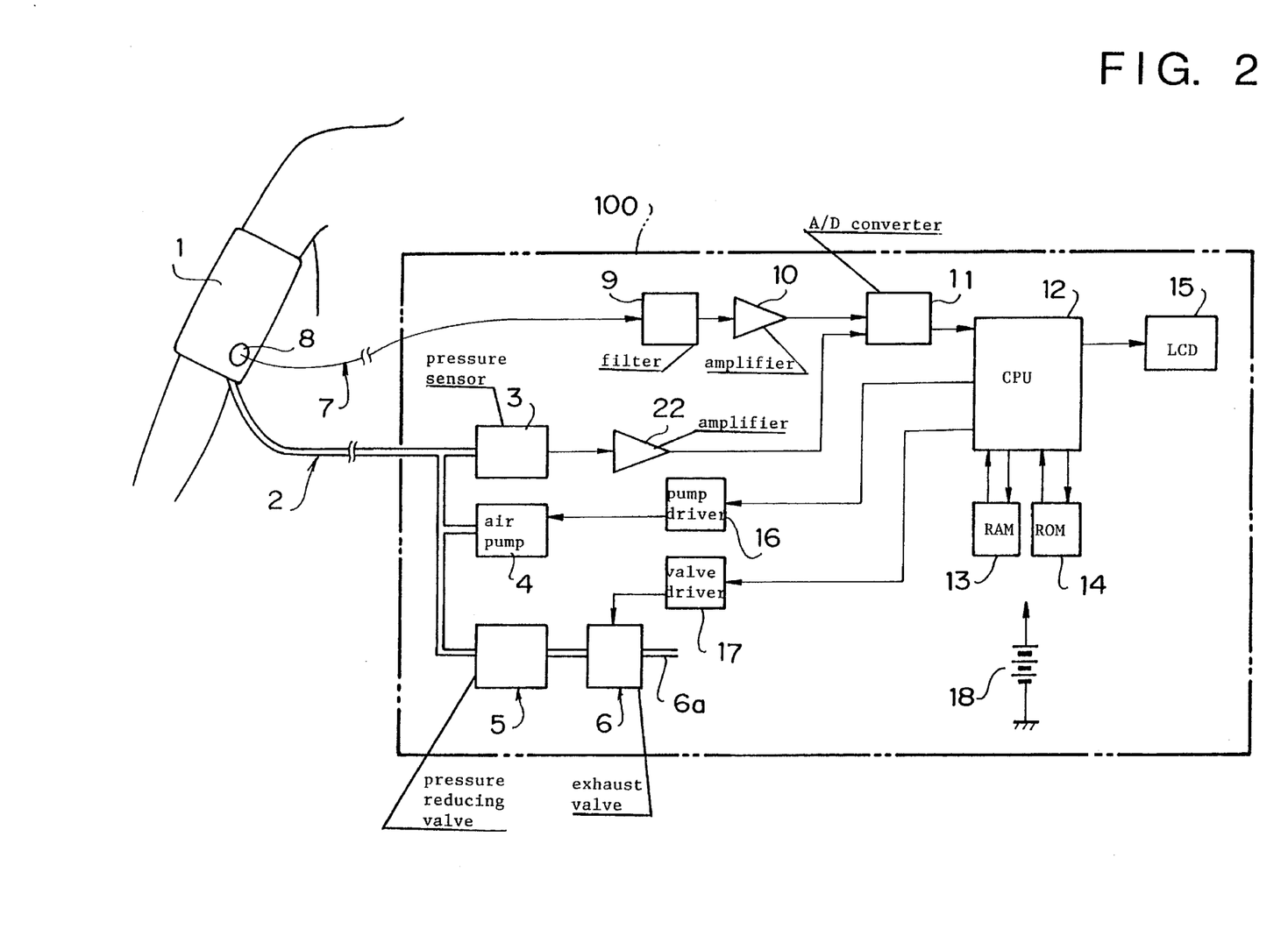
FIG. 2 is a block diagram of an automatic sphygmomanometer of an embodiment.

FIG. 2 is a block diagram of the automatic sphygmomanometer of the embodiment. As shown in FIG. 2, a compact case 100 indicated by a two-dot line contains units needed for automatic blood pressure measurement. A cuff 1 which controls a flow of blood includes a K-sound sensor 8 connected to a filter 9 (for discriminating K sounds) of the case 100 via a signal line 7, and is provided with an air tube 2 indicated by a double-line. In FIG. 2, the cuff 1 is set to the portion (a left arm) to be measured as an example.

In the case 100 of the automatic sphygmomanometer with the above arrangement, a pressure sensor 3, air pump 4, pressure reducing value 5, and exhaust valve 6 which are connected to the cuff 1 via the air tube 2 are provided.

A signal line 7 connected to the K-sound sensor 8 is further connected to a filter 9 for discriminating a K sound and an amplifier 10 for amplifying the K sound, and then to an A/D converter 11. The A/D converter 11 is also connected to an amplifier 22 connecting to the pressure sensor 3. The A/D converter 11 includes two channels for detecting K sounds in order to detect a pulse wave and pressure, and connects to an input port of CPU 12.

The CPU 12 connects to RAM 13, ROM 14, LCD (Liquid Crystal Display) 15, pump driver 16, and valve driver 17 respectively. The RAM 13 stores a detected K-sound, cuff pulse wave, and cuff pressure. The ROM 14 stores a measuring program and the relationship between the time of opening the exhaust valve and deflating pressure. The LCD 15 displays a predetermined information concerning maximum blood pressure and minimum blood pressure. Furthermore, the pump driver 16 connected to the air pump 4 and valve driver 17 connected to the exhaust valve 6 are connected to an output port of the CPU 12. Power is supplied by batteries 18 (usually two to four 1.5 V batteries), or other power source.

In the automatic sphygmomanometer with the above arrangement, the cuff 1 is inflated to a value higher than one's maximum blood pressure based on the blood pressure measuring method shown in FIG. 1, maximum and minimum blood pressure are measured, while the cuff pressure is released by the exhaust port 6a of the exhaust valve 6. In order to reduce the size and save energy to operate the exhaust valve 6 for releasing the air, the pressure reducing valve 5 has a function which automatically adjusts a cuff deflation rate regardless of the cuff pressure.

Figure 3:
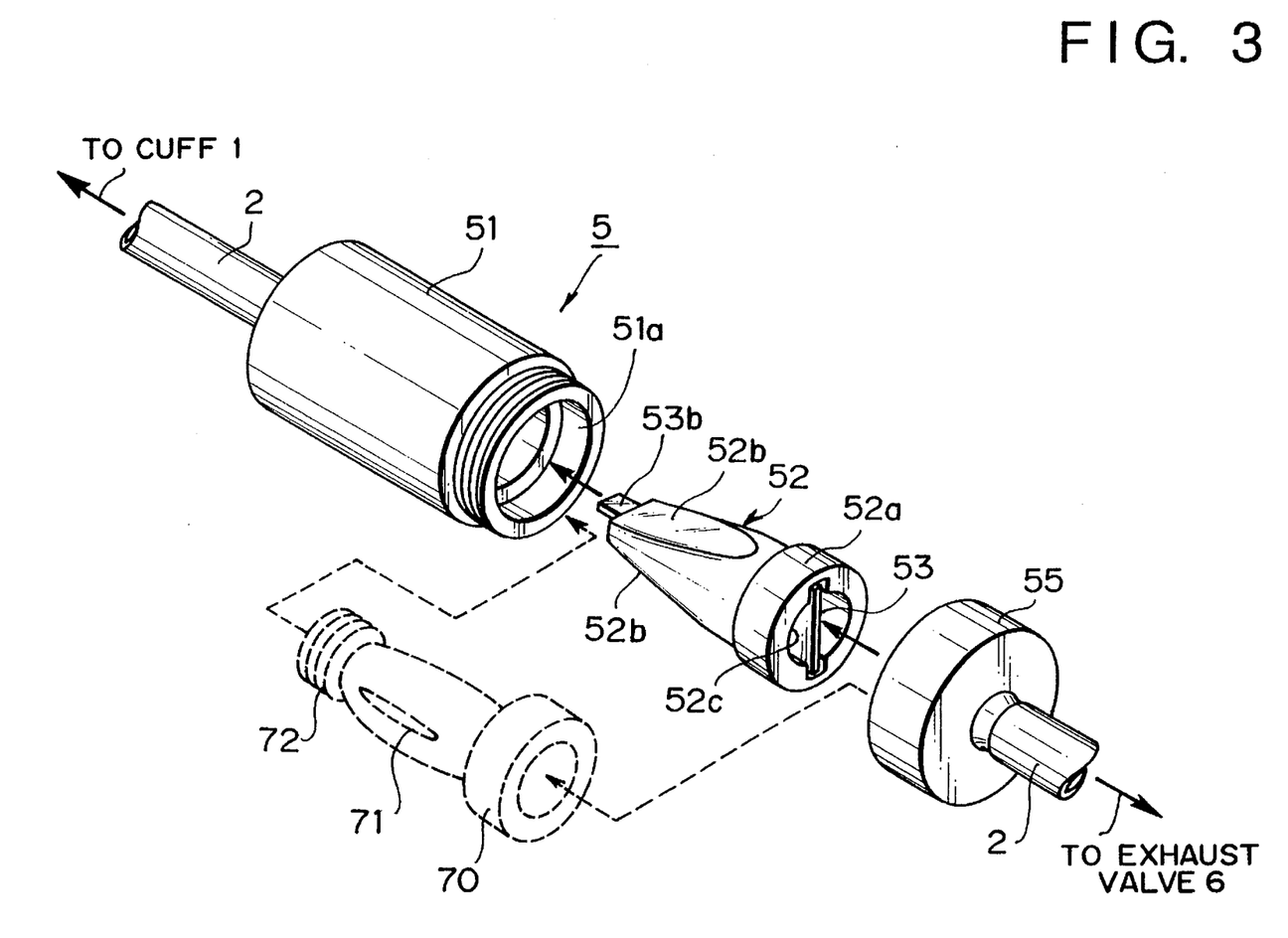
FIG. 3 is an exploded view of two examples of a constant-rate pressure reducing valve.

FIG. 3 is an exploded view showing two examples of the constructions of the pressure reducing valve 5. One is a valve 52 set up as indicated by an arrow of a solid line and the other is a valve 70 set up as indicated by a dotted line. The valve 52 is comprised of an elastic body such as rubber and pressure active surfaces 52b face each other so as to form a wedge. The valve 52 includes a hollow portion 52c and a slit in the hollow portion 52c. A flexible plate member 53 made from resin is twisted and inserted into the hollow portion 52c.

Figure 4:
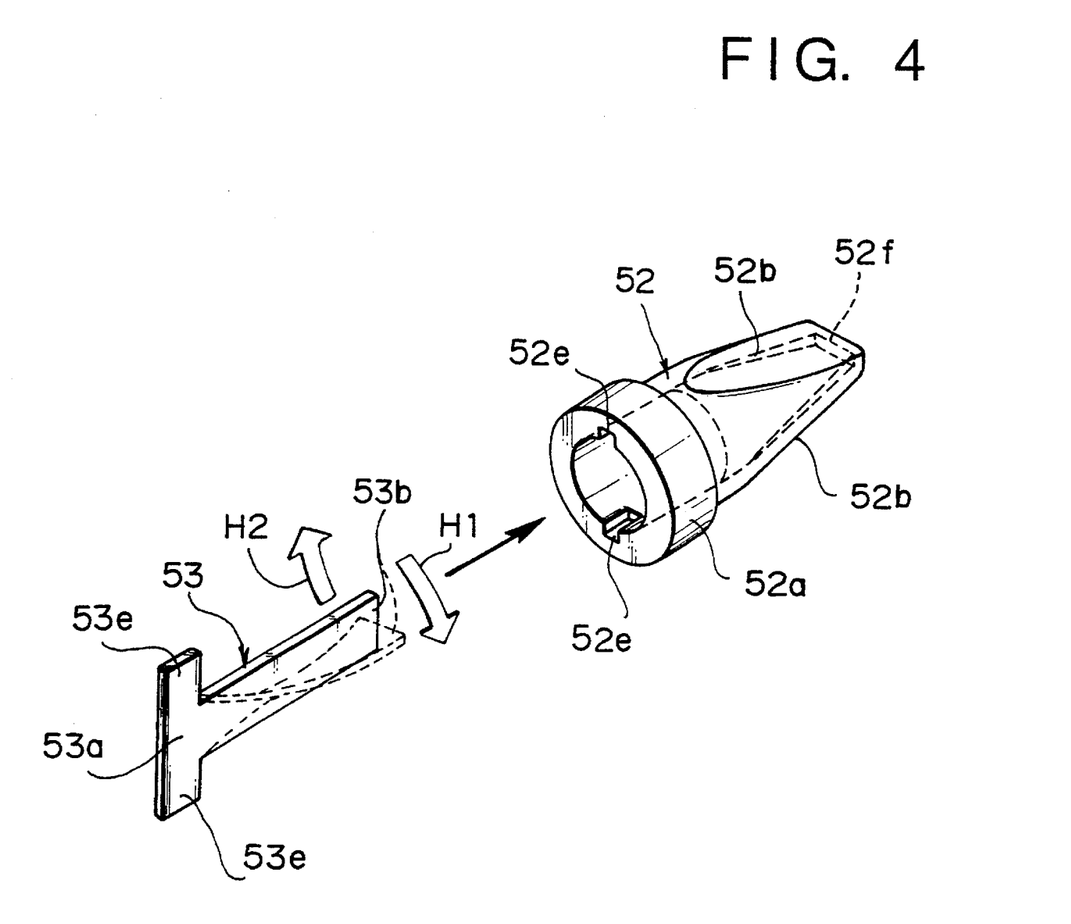
FIG. 4 is an exploded view of a pressure reducing valve.

As shown in FIG. 4, a leading end 53b of the flexible plate member 53 is inserted into a slit 52f of the valve 52 and the plate member 53 is twisted approximately 90 degree as indicated by a dotted line and both wings 53e of the plate member 53 are respectively inserted into grooves 52e. Thus, the valve 52 is constructed. As shown in FIG. 3, the pressure reducing valve 52 is set into a holder 51, an end of which is closed and fixed by a cap 55. The cap 55 is connected to the side of the exhaust valve 6, while the holder 51 is connected to the side of the cuff 1.

In the above construction, in the slit 52f of the valve 52 which is a flat opening of the valve made from rubber, a torsion resilience such that the plate member 53 returns to the original flat shape becomes active. Therefore, when the cuff pressure greatly effects the pressure active surfaces 52b, the slit 52f with a small opening maintains a constant rate for the pressure reduction. On the other hand, when the cuff pressure has less effect on the pressure active surfaces 52b, the opening area of the slit 52f becomes large and the cuff pressure and exhaustion pressure are balanced. With the above construction, a constant amount of air can be released regardless of the cuff pressure.

As shown in FIG. 3, in order to adjust the opening area of the slit 52f in accordance with the cuff pressure, the valve 70 (indicated by a broken line) comprising of a slit 71 and screwing portion 72 can be screwed into the holder 51.

Figure 5:
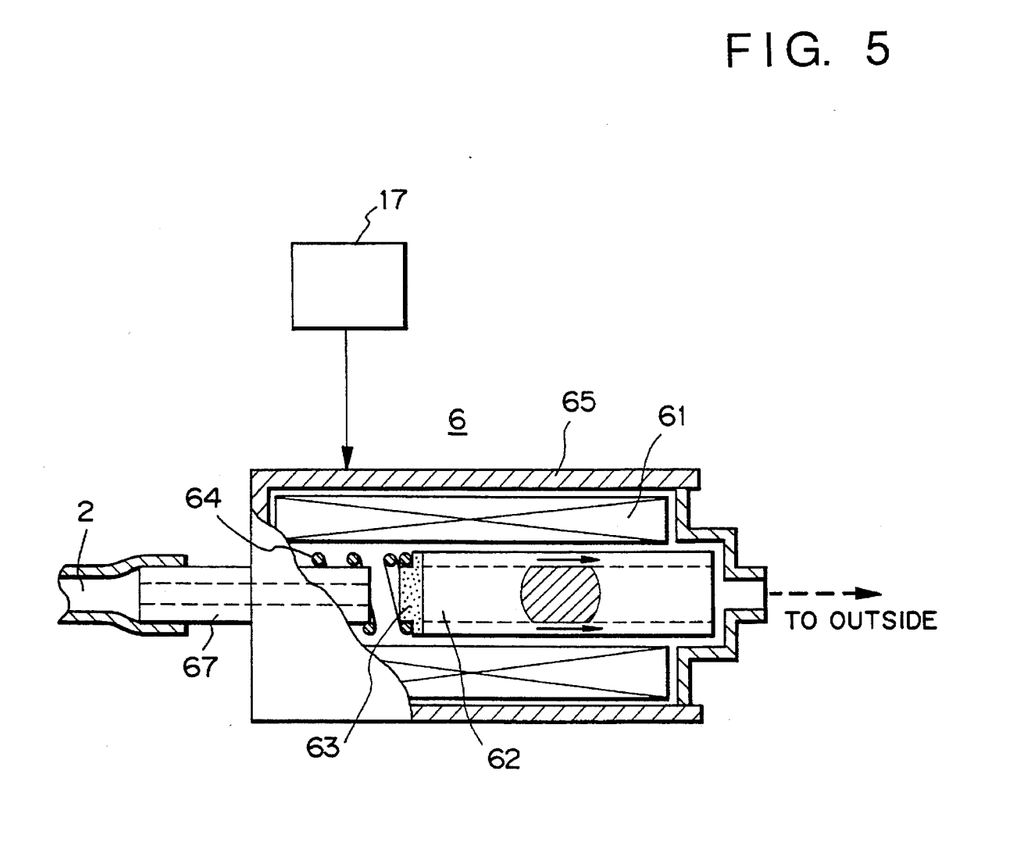
FIG. 5 is a partially cutaway view of an exhaust valve.

FIG. 5 is a partially cutaway view of the exhaust valve 6. A solenoid is formed by a coil 61 connected to the valve driver 17 and plunger 62 slidably retained in the coil 61. At the end of the plunger 62, a rubber packing 63 is opened so as to release the air by a spring 64 and is closed by electrifying. On the other hand, a slot (indicated by a broken line) of the plunger 62 is formed and opened when the power happens to be shut down. The exhaust valve 6 provided for the pressure reducing valve 5 for releasing the air can be small and power-saving type.

Figure 6:
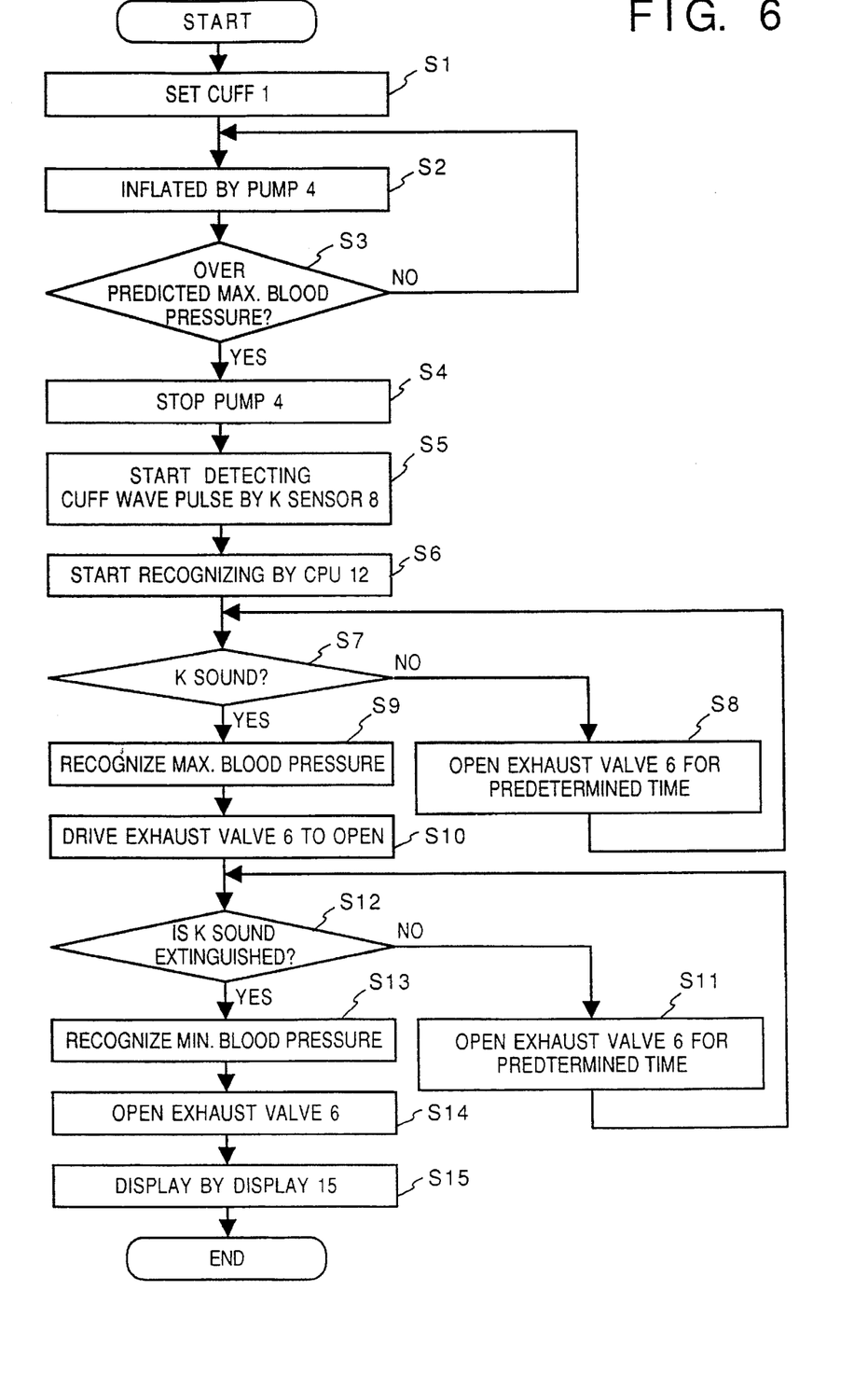
FIG. 6 is a flowchart of the control operation of the automatic sphygmomanometer.

Referring to the flowchart of FIG. 6, the operation of the automatic sphygmomanometer is described. When the blood pressure is measured, the cuff 1 is first set to a portion to be measured such as an arm or leg at step S1. At steps S2 and S3, a cuff pressure signal from the cuff sensor 3 is inputted to an A/D converter 11 via a DC amplifier 22 and converted to a digital value, the CPU 12 starts to measure a cuff pressure value, and the cuff 1 is inflated to a value higher than one's maximum blood pressure by a pump 4.

Subsequently, the inflation by the pump 4 is stopped at step S4, the process proceeds to step S5, and the CPU 12 recognizes a cuff pulse wave which is superimposed onto the cuff signal from the pressure sensor 3 (step S6).

Whether or not K sounds synchronizing with the cuff pulse wave exist is discriminated through the filter 9 and amplifier 10, and the result is inputted to the A/D converter 11 where the K sounds are converted to a digital value and recognized by the CPU 12 (step S6).

If it is determined that there are no K sounds at step S7, the exhaust valve 6 is opened by the valve driver 17 for an interval corresponding to a predetermined reducing pressure (e.g. 5 mm Hg) stored in the ROM 14 and closed after the predetermined period of time (step S8).

Subsequently, a cuff pulse wave from the pressure sensor is recognized, and if a K sound synchronizing with this wave is not detected, the operation for deflating the pressure is repeated at steps S7 and S8 and the result of the range A of FIG. 1 is obtained. On the other hand, at step S7, if the existence of K sounds is judged, the CPU 12 recognizes the pressure value at that time as a maximum blood pressure.

At step S10, in order to reduce the pressure a considerably large amount, which does not exceed the blood pressure stored in the ROM 14, the exhaust valve 6 is opened for an interval corresponding to the pressure reduction value. At step S11, the exhaust valve 6 is opened for releasing the air during the time interval when the exhaust valve is opened. At step S12, whether or not the K sound is extinguished is determined. The cuff pressure when the K sound finally can not be detected is determined as a minimum blood pressure at step S13. Subsequently, the process proceeds to step S14 where the exhaust valve is kept open and the cuff pressure is deflated to the atmospheric pressure. At step S15, the maximum blood pressure and minimum blood pressure are displayed by the LCD 15 and the blood pressure measurement ends.

As described above, according to the automatic sphygmomanometer of the present invention, each unit is contained in a limited space of the case and a small solenoid valve driven by low electric voltage can be used. Furthermore, a desired pressure reduction can be easily executed and pressure reduction control can be easily performed, since a constant reduction pressure can be obtained over the duration for opening the exhaust valve with a high cuff pressure to a relatively low cuff pressure.

As described above, according to an automatic sphygmomanometer of this invention, an energy-saving type automatic sphygmomanometer capable of measuring a blood pressure in a deflating process after the cuff pressure is inflated to one's maximum blood pressure and where the sphygmomanometer size can be reduced is provided.

As many apparently widely different embodiments of the present invention can be made without departing from the spirit and scope thereof, it is to be understood that the invention is not limited to the specific embodiments thereof except as defined in the appended claims.

What is claimed is:

1. An automatic sphygmomanometer which inflates a cuff to a cuff pressure higher than an individual's maximum blood pressure and measures a blood pressure in a deflating process, comprising:
    a pressure cuff for being placed on a portion of an individual's body;
    air pressurization means connected to said pressure cuff to pressurize the cuff by pumping air into the cuff;
    a pressure reducing valve connected to the cuff, said pressure reducing valve having an inlet side connected to the pressure cuff and an exhaustion side;
    an openable and closable exhaust valve connected to the exhaustion side of said pressure reducing valve to intermittently exhaust air delivered from the pressure reducing valve, the pressure reducing valve automatically adjusting a cuff pressure reducing exhaust rate to a substantially constant rate regardless of the cuff pressure when the exhaust valve is opened;
    control means for controlling opening and closing of the exhaust valve; and
    measuring means connected to the pressure cuff for measuring the individual's blood pressure.

2. The automatic sphygmomanometer according to claim 1, wherein the measuring means includes a pressure sensor, the blood pressure measurement being performed by detecting Korotkoff sounds.

3. The automatic sphygmomanometer according to claim 1, wherein said air pressurization means is an electric-powered pump whose power is supplied from a battery.

4. The automatic sphygmomanometer according to claim 1, wherein said exhaust valve is comprised of a solenoid as a driving source, whose power is supplied from a battery.

5. The automatic sphygmomanometer according to claim 4, wherein said exhaust valve includes means for preventing exhaustion of air from the cuff when electric power is supplied from the battery and for allowing exhaustion of air from the cuff when electric power is not supplied.

6. The automatic sphygmomanometer according to claim 1, wherein said pressure reducing valve is comprised of:
    a container connected to a tube, the tube being connected to the cuff;
    a lid member connected to said exhaust valve for covering the container; and
    elastic member including:
        a retainer portion for retaining the elastic member in a predetermined location of the container; and
        a slit that opens relatively little when the cuff pressure is large and that opens relatively widely when the cuff pressure is small.

7. The automatic sphygmomanometer according to claim 6, wherein said elastic member includes slant surfaces that face one another, said slit being formed at one end of the slant surfaces, and said pressure reducing valve including a plate member having a tongue portion and a base, said plate member being twisted with the tongue portion fitted into said slit.

8. The automatic sphygmomanometer according to claim 6, wherein said slit is formed along the longitudinal direction on an outer surface of the elastic member which is narrowed toward the cuff.

9. The automatic sphygmomanometer according to claim 1, wherein said inlet side of the pressure reducing valve is directly connected to the pressure cuff and the exhaust valve is directly connected to the exhaustion side of the pressure reducing valve.

10. The automatic sphygmomanometer according to claim 1, wherein said exhaust valve is arranged in series with respect to said pressure reducing valve.

11. An automatic sphygmomanometer which inflates a cuff to a cuff pressure higher than an individual's maximum blood pressure and measures a blood pressure by detecting Korotkoff sounds in a deflating process, comprising:
    a pressure cuff for placement on a portion of an individual's body;
    air pressurization means connected to the pressure cuff for inflating the pressure cuff, said air pressurization means including an electric pump connected to a battery to provide electric power to the pump;

an openable and closable exhaust valve connected to said cuff and driven by a solenoid in order to exhaust air intermittently from said cuff to reduce a cuff pressure in the cuff;

pressure reducing means for automatically adjusting a cuff pressure reducing exhaust rate to a substantially constant rate regardless of the cuff pressure when said exhaust valve is opened, said pressure reducing means having an exhaustion side connected to the exhaust valve through which air is exhausted from the pressure reducing means;

control means for controlling opening and closing of said exhaust valve;

measuring means connected to the pressure cuff for measuring the individual's blood pressure; and a display connected to the measuring means for displaying results of the blood pressure measurement.

12. The automatic sphygmomanometer according to claim 11, wherein said exhaust valve includes a valve mechanism for preventing exhaustion of air from the cuff when electric power is supplied from a battery and for allowing exhaustion of air from the cuff when electric power is not supplied.

13. The automatic sphygmomanometer according to claim 11, wherein said pressure reducing means is comprised of:

a container connected to a tube, the tube being connected to the cuff;

a lid member connected to said exhaust valve for covering the container; and an elastic member including:
 a retainer portion for retaining the elastic member in a predetermined location of the container; and
 a slit that opens relatively little when the cuff pressure is large and that opens relatively widely when the cuff pressure is small.

14. The automatic sphygmomanometer according to claim 13, wherein said elastic member includes slant surfaces which face one another, said slit being formed at one end of the slant surfaces, and said pressure reducing means including a plate member having a tongue portion and a base, said plate member being twisted with the tongue portion fitted into said slit.

15. The automatic sphygmomanometer according to claim 13, wherein said slit is formed along the longitudinal direction on an outer surface of the elastic member which is narrowed toward the cuff.

16. A method of measuring an individual's blood pressure comprising:

placing a cuff on a portion of an individual's body;

inflating the cuff to a cuff pressure higher than an individual's maximum blood pressure by an electric pump to which electric power is supplied by a battery;

controlling an exhaust valve through operation of a solenoid supplied with power from a battery;

exhausting air intermittently from the cuff by opening the exhaust valve for a predetermined interval, the air being intermittently exhausted via a pressure reducing valve which automatically adjusts a cuff pressure reducing air rate to a substantially constant rate regardless of the cuff pressure;

measuring the individual's blood pressure by detecting Korotkoff sounds during cuff pressure reduction; and displaying the result of the blood pressure measurement on a display.

17. The method according to claim 16, including detecting an existence of Korotkoff sounds while opening said exhaust valve in predetermined intervals in an exhaustion step subsequent to said inflating step to measure a maximum blood pressure, detecting non-existence of Korotkoff sounds while opening said exhaust valve in predetermined intervals to measure a minimum blood pressure, and showing the result of the blood pressure measurement on the display.

18. The method according to claim 16, including reducing the pressure in said cuff is in a stepwise manner.

* * * * *

UNITED STATES PATENT AND TRADEMARK OFFICE
CERTIFICATE OF CORRECTION

PATENT NO. : 5,467,772

DATED : November 21, 1995

INVENTOR(S) : Takahiro SOUMA

It is certified that error appears in the above-indentified patent and that said Letters Patent is hereby corrected as shown below:

In Column 3, line 61, delete "a".

In Column 3, line 61, after "concerning" insert --a--.

In Column 8, line 39, delete "is".

Signed and Sealed this

Twenty-eighth Day of May, 1996

Attest:

BRUCE LEHMAN

*Attesting Officer*          *Commissioner of Patents and Trademarks*